United States Patent [19]

Devant et al.

[11] Patent Number: 5,103,025
[45] Date of Patent: Apr. 7, 1992

[54] PROCESS FOR THE RESOLUTION OF ENANTIOMERS OF BENZOPYRAN DERIVATIVES

[75] Inventors: Ralf Devant, Darmstadt; Rolf Gericke, Seeheim, both of Fed. Rep. of Germany

[73] Assignee: Merck Patent Gesellschaft Mit Beschrankter Haftung, Darmstadt, Fed. Rep. of Germany

[21] Appl. No.: 608,442

[22] Filed: Nov. 2, 1990

[30] Foreign Application Priority Data

Nov. 3, 1989 [DE] Fed. Rep. of Germany ....... 3936616

[51] Int. Cl.$^5$ .......................................... C07D 311/78
[52] U.S. Cl. .................................................... 549/387
[58] Field of Search ......................................... 549/387

[56] References Cited

FOREIGN PATENT DOCUMENTS 2204868 11/1988 United Kingdom .

Primary Examiner—Nicky Chan
Attorney, Agent, or Firm—Millen, White & Zelano

[57] ABSTRACT

The invention relates to a process for the resolution of enantiomers of 3,4-epoxy-3,4-dihydro-2,2-dimethyl-3-R-2H-1-benzopyran-6-carbonitriles (I), in which R is H or CH$_3$, characterized in that racemic I is dissolved in an inert solvent or solvent mixture together with a small amount of (−)−I [or (+)−I], the solution is seeded with (−)−I [or (+)−I], the precipitated (−)−I [or (+)−I] is isolated, further racemic I is dissolved in the filtrate, seeded with (+)−I [or (−)−I], the precipitated (+)−I [or (−)−I] is isolated and, if desired, this crystallization cycle is repeated one or more times.

16 Claims, No Drawings

PROCESS FOR THE RESOLUTION OF ENANTIOMERS OF BENZOPYRAN DERIVATIVES

SUMMARY OF THE INVENTION

The invention relates to a process for the resolution of enantiomers of 3,4-epoxy-3,4-dihydro-2,2-dimethyl-3-R-2H-1-benzopyran-6-carbonitriles (2,2-dimethyl-1-3-R-3,4-epoxy-6-cyanochromans; "I")

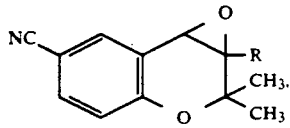

in which R is H or $CH_3$.

The compounds I include the preferred 3,4-epoxy-3,4-dihydro-2,2,-dimethyl-2H-1-benzopyran-6-carbonitrile (Ia) and 3,4-epoxy-3,4-dihydro-2,2,3-trimethyl-2H-1-benzopyran-6-carbonitrile (Ib).

Racemic Ia and its two enantiomers, (+)-Ia and (−)-Ia, are disclosed in GB-A-2,204,868. According to the information given there, (+)-Ia and (−)-Ia are obtainable by esterifying trans-3-bromo-4-hydroxy-2,2-dimethyl-2H-1-benzopyran-6-carbonitrile with (−)camphanic acid, separating the resulting diastereomer mixture by chromatography and hydrolyzing the two diastereomers using alkali, whereupon closure of the epoxide ring takes place simultaneously with elimination of HBr.

Racemic Ib (m.p. 118°) and its two enantiomers, (+)-Ib and (−)-Ib, are analogously obtainable from trans-3-bromo-4-hydroxy-2,2,3-trimethyl-2H-1-benzopyran-6-carbonitrile which, in turn, can be prepared in a conventional manner from 3-acetyl-4-hydroxybenzonitrile via 2,2-dimethyl-6-cyano-4-chromanone (m.p. 119°-120°), 2,2-dimethyl-3-methylene-6-cyano-4-chromanone, 2,2,3-trimethyl-6-cyano-4-chromanol and 2,2,3-trimethyl-6-cyano-2H-chromene (m.p. 55°).

In practice, the processes given for the chemical resolution of enantiomers have great disadvantages, as expensive auxiliary reagents are necessary, and the resolution requires two additional chemical reactions.

An object of the invention is a process for the resolution of enantiomers of I which does not have, or only has to a small extent, the disadvantages of these processes.

Upon further study of the specification and appended claims, further objects and advantages of this invention will become apparent to those skilled in the art.

These objects are achieved by the discovery of the present process of crystallization by entrainment.

The invention accordingly relates to a process for the resolution of enantiomers of I, characterized in that racemic I is dissolved in an inert solvent or solvent mixture together with a small amount of (−)-I [or (+)-I], the solution is seeded with (−)-I [or (+)-I], the precipitated (−)-I [or (+)-I] is isolated, further racemic I is dissolved in the filtrate, seeded with (+)-I [or (−)-I], the precipitated (+)-I [or (−)-I] is isolated and, if desired, this crystallization cycle is repeated one or more times.

As a rule, this entrainment process cannot be used for the resolution of racemic compounds. It is therefore surprising that it can be used with success in the case of I.

Suitable solvents are preferably ethers such as tetrahydrofuran or methyl tert.-butyl ether, lower alcohols which contain 1-4 C atoms, in particular isopropanol, or mixtures of lower alcohols with hydrocarbons, for example, isopropanol/hexane, or of halogenated hydrocarbons with hydrocarbons, for example dichloromethane/hexane. Tetrahydrofuran is particularly preferred.

In detail, racemic I is dissolved together with about 1.5-2.5% by weight of (−)- or (+)-I, preferably in the presence of heat, in about 1-2 volumes (for example, 1 ml, relative to 1 g of I) of tetrahydrofuran, cooled and seeded with a trace (for example, about 0.004-0.1% by weight) of pure (−)-I [or (+)-I]. The crystallized (−)-I [or (+)-I] is isolated, preferably filtered off. A further amount of the racemate, which corresponds to the amount of the enantiomer previously filtered off, is preferably added to the filtrate, and the added material is dissolved in the presence of heat. Renewed cooling and seeding with (+)-I [or (−)-I], i.e., the other enantiomer, causes crystallization of (+)-I [or (−)-I] which is also isolated, preferably filtered off. This crystallization cycle can be repeated one or more times by dissolving further racemic I in the filtrate finally obtained, causing further (−)-I [or (+)-I] to crystallize by cooling and seeding, dissolving racemic I again in the filtrate from this and obtaining further (+)-I [or (−)-I] by cooling and seeding, etc.

This embodiment is distinguished in that, in contrast to customary crystallization processes, crystallization takes place from very concentrated solution.

Without further elaboration, it is believed that one skilled in the art can, using the preceding description, utilize the present invention to its fullest extent. The following preferred specific embodiments are, therefore, to be construed as merely illustrative, and not limitative of the remainder of the disclosure in any way whatsoever.

In the foregoing and in the following examples, all temperatures are set forth uncorrected in degrees Celsius and unless otherwise indicated, all parts and percentages are by weight.

The entire disclosures of all applications, patents and publications, cited above and below, and of corresponding application Federal Republic of Germany P 39 36 616.2, filed Nov. 3, 1989, are hereby incorporated by reference.

EXAMPLES

EXAMPLE 1

475 g of racemic Ia and 5 g of pure (−)-Ia are dissolved at 35° in 700 ml of tetrahydrofuran. The solution is allowed to cool to 17. with stirring and is seeded with 20 mg of pure (−)-Ia. After 4 hours, 29 g of (−)-Ia are filtered off; optical purity 92% ee (i.e., enantiomeric excess).

29 g of racemic Ia are added to the mother liquor with warming and are dissolved by stirring. After renewed cooling to 17°, the solution is seeded with 20 mg of pure (+)-Ia. After 4 hours, 31 g of (+)-Ia are filtered off; optical purity 90% ea.

The crystallization cycle can be repeated several times.

By repeated recrystallization of the enantiomers obtained in this way from isopropanol, products having an enantiomeric purity of ≧99% ee are obtained:

(−)-enantiomer, m.p. 141°-142°; $[\alpha]_D^{25}$ −92.5° (c=1 in methanol)

(+)-enantiomer, m.p. 141°-142°; $[\alpha]_D^{25}$ +91.7° (c=1 in methanol)

The optical purity can be determined by means of differential scanning calorimetry (DSC) or, alternatively, by HPLC chromatography after reaction with (S)-1-phenylethylamine to give the diastereomeric 3,4-dihydro-3-hydroxy-2,2-dimethyl-4-(1-phenylethylamino)-2H-benzopyran-6-carbonitriles.

EXAMPLE 2

The following are obtained from racemic Ib analogously to Example 1

(−)-Ib, m.p. 153°-155°; $[\alpha]_D^{25}$ −135.2° (c=1 in methanol) and (+)-Ib, m.p. 153°-155°; $[\alpha]_D^{25}$ +135.2° (c=1 in methanol)

The preceding examples can be repeated with similar success by substituting the generically or specifically described reactants and/or operating conditions of this invention for those used in the preceding examples.

From the foregoing description, one skilled in the art can easily ascertain the essential characteristics of this invention, and without departing from the spirit and scope thereof, can make various changes and modifications of the invention to adapt it to various usages and conditions.

What is claimed is:

1. A process for resolving the enantiomers of 3,4-epoxy-3,4-dihydro-2,2-dimethyl-3-R-2H-1-benzopyran-6-carbonitrile (I), wherein R is H or $CH_3$, comprising:
   (a) dissolving a racemic (I) together with a small amount of either the (−)-enantiomer or (+)-enantiomer of said racemic (I) in an inert solvent or solvent mixture;
   (b) seeding the solution of step (a) with the enantiomer employed in step (a);
   (c) isolating the enantiomer which was used to seed the solution in step (b);
   (d) adding additional amount of said racemic (I) to said solution;
   (e) seeding the solution of step (d) with the enantiomer which is not employed in the previous seeding step;
   (f) isolating the enantiomer which was used to seed the solution in step (e); and
   (g) repeating the cycle of steps (d)-(f) one or more times, alternating the enantiomer of said racemic (I) used in step (e) between the (+)-enantiomer and the (−)-enantiomer.

2. A process according to claim 1, wherein said solvent is tetrahydrofuran, methyl tert-butylether, or a $C_{1-4}$-alcohol.

3. A process according to claim 1, wherein said solvent mixture is a mixture of a $C_{1-4}$-alcohol with a hydrocarbon or is a mixture of halogenated hydrocarbon with hydrocarbons.

4. A process according to claim 2, wherein said solvent is isopropanol.

5. A process according to claim 2, wherein said solvent is tetrahydrofuran.

6. A process according to claim 3, wherein said solvent mixture is a mixture of isopropanol and hexane or is a mixture of dichloromethane and hexane.

7. A process according to claim 1, wherein said racemic (I) is initially dissolved with about 1.5-2.5 wt. % of the (−)-enantiomer or (+)-enantiomer and about 1-2 vol. of tetrahydrofuran.

8. A process according to claim 1, wherein, prior to being seeded with the enantiomer, said solution is cooled.

9. A process according to claim 1, wherein said solution is seeded with about 0.004-0.1 wt. % of the enantiomer.

10. A process according to claim 1, wherein the amount of said racemic (I) added following each isolation step corresponds approximately to the amount of enantiomer isolated in said isolation step.

11. A process according to claim 1, wherein dissolution occurs in the presence of heat.

12. A process according to claim 1, wherein isolation occurs by filtration.

13. A process according to claim 1, wherein R is H.

14. A process according to claim 1, wherein R is $CH_3$.

15. A process for resolving the enantiomers of 3,4-epoxy-3,4-dihydro-2,2-dimethyl-3-R-2H-1-benzopyran-6-carbonitrile (I), wherein R is H or $CH_3$, comprising:
    isolating either the (−)-enantiomer or (+)-enantiomer of a racemic (I) from a solution, said solution containing said racemic (I) and a small amount of that enantiomer which is to be isolated in an inert solvent or solvent mixture, wherein said solution has previously been seeded with the enantiomer to be isolated.

16. A process for resolving the enantiomers of 3,4-epoxy-3,4-dihydro-2,2-dimethyl-3-R-2H-1-benzopyran-6-carbonitrile (I), wherein R is H or $CH_3$, comprising:
    dissolving a racemic (I) together with a smaller amount of either the (−)- enantiomer of said racemic (I) or the (+)-enantiomer of said racemic (I) in an inert solvent or solvent mixture;
    seeding the resulting solution with the enantiomer employed in the previous step;
    isolating the resultant precipitated enantiomer;
    dissolving an additional amount of said racemic (I) in said solution;
    seeding said solution with the other enantiomer of said racemic (I); and isolating the precipitated enantiomer.

* * * * *